US011976024B2

(12) United States Patent
Farid et al.

(10) Patent No.: US 11,976,024 B2
(45) Date of Patent: May 7, 2024

(54) PROCESS FOR PREPARING CYANOACETATES

(71) Applicant: Henkel AG & Co. KGaA, Duesseldorf (DE)

(72) Inventors: Umar Farid, County Dublin (IE); Jessica Ramos, County Kildare (IE); Michael Thai Trung King, County Dublin (IE); Justine O'Sullivan, County Kildare (IE); Isidro Cobo Cardenete, County Dublin (IE); Ciara Goff, County Wexford (IE); Cormac Duffy, County Louth (IE); Marisa Phelan, County Dublin (IE); Barry Burns, County Dublin (IE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 17/838,897

(22) Filed: Jun. 13, 2022

(65) Prior Publication Data

US 2022/0315526 A1    Oct. 6, 2022

Related U.S. Application Data

(63) Continuation of application No. PCT/EP2020/085136, filed on Dec. 8, 2020.

(30) Foreign Application Priority Data

Dec. 12, 2019  (GB) ..................................... 1918325

(51) Int. Cl.
| | | |
|---|---|---|
| *C07C 253/30* | (2006.01) | |
| *C07C 227/18* | (2006.01) | |
| *C07C 253/08* | (2006.01) | |
| *C07C 253/14* | (2006.01) | |

(52) U.S. Cl.
CPC .......... *C07C 253/30* (2013.01); *C07C 227/18* (2013.01); *C07C 253/08* (2013.01); *C07C 253/14* (2013.01)

(58) Field of Classification Search
CPC .................................................. C07C 253/30
See application file for complete search history.

(56) References Cited

U.S. PATENT DOCUMENTS

| | | | |
|---|---|---|---|
| 2,721,858 A | 10/1955 | Joyner et al. | |
| 2,756,251 A | 7/1956 | Joyner et al. | |
| 2,763,677 A | 9/1956 | Jeremias | |
| 4,202,920 A | 5/1980 | Margotte et al. | |
| 4,364,876 A | 12/1982 | Kimura et al. | |
| 4,438,041 A * | 3/1984 | Matsui .................. | C07C 255/00 558/406 |
| 4,512,357 A | 4/1985 | Earl | |
| 5,624,699 A | 4/1997 | Lang | |
| 6,245,933 B1 * | 6/2001 | Malofsky .............. | C07C 253/30 558/375 |
| 10,822,303 B2 * | 11/2020 | Duffy .................... | B01J 21/066 |
| 10,913,708 B2 * | 2/2021 | Duffy ...................... | B01J 23/20 |

FOREIGN PATENT DOCUMENTS

| | | |
|---|---|---|
| EP | 0459617 | 12/1991 |
| EP | 1099701 | 5/2001 |
| WO | 2008156726 | 12/2008 |

OTHER PUBLICATIONS

Senchenya et al., Russian Chem. Bull., 42, 5, 909 (1993).
Guseva et al., Russian Chem. Bull., 43, 4, 595 (1994).
Golobolov and Gruber, Russian Chem. Rev., 66, 11, 953 (1997).
Guseva et al., Russian Chem. Bull., 42, 3, 478 (1993).
Vijayalakshi et al., J. Ad. Sci. Technol., 4, 9, 733 (1990).
Renner et al., Cure of Epoxy Resins with Esters of Cyanoacrylic Acid, J. Polym. Sci., Polym. Chem. Ed., 23, 2341 (1985).
PCT International Search Report issued in connection with International Application No. PCT/EP2020/085136—Mailing date: Mar. 30, 2021.
M. Yamauchi: "Facile Conversion of Acetals to Nitriles", Chemical and Pharmaceutical Bulletin, vol. 41, No. 11, pp. 2042-2043 (1993).
Findlay et al., A facile one-step conversion of aliphatic aldehydes into nitriles, Canadian Journal of Chemistry, vol. 45, No. 9, pp. 1014-1015 (1967).

* cited by examiner

*Primary Examiner* — Golam M Shameem
(74) *Attorney, Agent, or Firm* — Steven C. Bauman

(57) ABSTRACT

This invention relates to a process for producing cyanoacetates involving contacting a salt of an alkyl, alkenyl, alkynyl or aryl formyl acetate with a hydroxyl amine acid under appropriate conditions and for a time sufficient to yield a cyanoacetate.

19 Claims, No Drawings

PROCESS FOR PREPARING CYANOACETATES

BACKGROUND

Field

This invention relates to a process for producing cyanoacetates involving contacting a salt of an alkyl, alkenyl, alkynyl or aryl formyl acetate with a hydroxyl amine acid under appropriate conditions and for a time sufficient to yield a cyanoacetate.

Brief Description of Related Technology

Cyanoacrylate adhesives are known for their fast adhesion and ability to bond a wide variety of substrates. They are marketed as "super glue" type adhesives. They are useful as an all-purpose adhesive since they are a single component adhesive, very economical as only a small amount will do, and generally do not require any equipment to effectuate curing.

Traditionally, cyanoacrylate monomers have been produced by way of a Knoevenagel condensation reaction between a formaldehyde precursor, such as paraformaldehyde, and an alkyl cyanoacetate with a basic catalyst. During the reaction, cyanoacrylate monomer forms and polymerises in situ to a prepolymer. The prepolymer is subsequently thermally cracked or depolymerised, yielding cyanoacrylate monomer. This approach has remained essentially the same over time, though various improvements and variants have been introduced. See e.g. U.S. Pat. Nos. 6,245,933, 5,624,699, 4,364,876, 2,721,858, 2,763,677 and 2,756,251. Thus, it is seen one use of cyanoacetates is in the formation of cyanoacrylates.

Vijayalakshmi et al., *J. Ad. Sci. Technol.*, 4, 9, 733 (1990) describes some approaches to the synthesis of cyanoacetates and corresponding cyanoacrylates, including preparation from chloroacetic acid and its esters by subsequent reaction with sodium cyanide.

Guseva et al., *Russian Chem. Bull.*, 42, 3, 478 (1993) describes functionalized cyanoacetates, many of which were used in the subsequent synthesis of corresponding cyanoacrylates. [See also Guseva et al., *Russian Chem. Bull.*, 43, 4, 595 (1994), and Golobolov and Gruber, *Russian Chem. Rev.*, 66, 11, 953 (1997).] Cyanoacetates with siliconised functionalities have been described. See e.g. Senchenya et al., *Russian Chem. Bull.*, 42, 5, 909 (1993) and European Patent Document No. EP 0 459 617.

The preparation of mono-, di-, tri- and tetra-functional cyanoacetates, albeit as curatives for epoxy resins for adhesive applications, has been described. Renner et al., "Cure of Epoxy Resins with Esters of Cyanoacrylic Acid", *J. Polym. Sci., Polym. Chem. Ed.*, 23, 2341 (1985) and U.S. Pat. Nos. 4,202,920 and 4,512,357.

It would be desirable to find alternative synthetic approaches to making cyanoacetates, particularly if such approaches used readily available and inexpensive starting materials. It would be even more desirable if such approaches generated the subject cyanoacetate in high yield and was readily isolated.

SUMMARY

At a high level, the inventive process provides for the preparation of a cyanoacetate. This process in one aspect uses two steps. The first is the contacting of an alkyl, alkenyl, alkynyl or aryl acetate with an alkyl, alkenyl, alkynyl or aryl formate in the presence of a base and for a time sufficient to form a salt of an alkyl, alkenyl, alkynyl or aryl formyl acetate. The second is the contacting of the so formed salt of the alkyl, alkenyl, alkynyl or aryl formyl acetate with a hydroxyl amine acid under appropriate conditions and for a time sufficient to yield a cyanoacetate.

Optionally, after one or each of these steps a separation step may be performed. After the first step the so-formed salt of an alkyl, alkenyl, alkynyl or aryl formyl acetate may be separated from the reactants and/or any by-products. After the second step, the so formed cyanoacetate may be separated from the reactants and/or any by-products.

More specifically, and in a particularly desirable embodiment, the first step reacts ethyl formate in the presence of a base (such as sodium or potassium hydride or a sodium or potassium alkoxide) with an alkyl acetate (such as ethyl acetate) under appropriate conditions and for a time sufficient to yield an ethyl-3-oxopropanoate enol salt. The enol salt may optionally be separated prior to use to form ethyl cyanoacetate. Whether or not separated, the ethyl-3-oxopropanoate enol salt may be reacted with ammonium hydroxide hydrochloride to yield the ethyl cyanoacetate.

In another aspect, the inventive method may be conducted in one step. Here, an alkyl, alkenyl, alkynyl or aryl acetate is contacted with an alkyl, alkenyl, alkynyl or aryl formate under basic conditions and for a time sufficient to form a salt of an alkyl, alkenyl, alkynyl or aryl formyl acetate, and after which a hydroxyl amine acid is mixed therewith under appropriate conditions and for a time sufficient to yield a cyanoacetate.

And in another aspect, the inventive method may be conducted in one step, where a salt of an alkyl, alkenyl, alkynyl or aryl formyl acetate is contacted with a hydroxyl amine acid under appropriate conditions and for a time sufficient to yield a cyanoacetate. Optionally, separating therefrom the so formed cyanoacetate.

DETAILED DESCRIPTION

As noted above, in one aspect, the present invention provides a process for the preparation of a cyanoacetate, steps of which comprise:

(a) contacting an alkyl, alkenyl, alkynyl or aryl acetate with an alkyl, alkenyl, alkynyl or aryl formate in the presence of a base and for a time sufficient to form a salt of an alkyl, alkenyl, alkynyl or aryl formyl acetate;

(b) optionally, separating therefrom the so formed salt of an alkyl, alkenyl, alkynyl or aryl formyl acetate;

(c) contacting the alkyl, alkenyl, alkynyl or aryl formyl acetate with a hydroxyl amine acid under appropriate conditions and for a time sufficient to yield a cyanoacetate;

(d) optionally, separating therefrom the so formed cyanoacetate.

The alkyl, alkenyl, alkynyl or aryl acetate may be selected from any one or more of the following alkyl acetates: methyl acetate, ethyl acetate, propyl acetates, butyl acetates, pentyl acetates, hexyl acetates, heptyl acetates, or octyl acetates, to name a few; the following alkenyl acetate: allyl acetate, as an example; the following alkynyl acetate: ethynyl acetate, as an example; or the following aryl acetates: phenyl acetate, benzyl acetate, or phenethyl acetate, to name a few.

The alkyl, alkenyl, alkynyl or aryl acetate should be used in an amount of about 0.5 to about 5, such as about 1 to about 3.5 molar equivalents.

The alkyl, alkenyl, alkynyl or aryl formate be selected from methyl formate, ethyl formate, propyl formates, butyl formates, pentyl formates, hexyl formates, heptyl formates, or octyl formates, to name a few; the following alkenyl formate: allyl formate, as an example; the following alkynyl formate: ethynyl formate, as an example; or the following aryl formates: phenyl formate, benzyl formate, or phenethyl formate, to name a few.

The alkyl, alkenyl, alkynyl or aryl formate should be used in an amount of about 0.5 to about 2.0 molar equivalents.

The base used in step (a) above should be a Group I metal cation (such as sodium or potassium) associated with an anion (such as hydride or alkoxide like methoxy or ethoxy).

The base should be used in an equimolar amount to an excess relative to either or both individually of the alkyl, alkenyl, alkynyl or aryl acetate and the alkyl, alkenyl, alkynyl or aryl formate.

The appropriate conditions may comprise the use of an organic polar solvent, such as an organic polar aprotic solvent. Desirable choices for such a solvent are ethers, such as dialkyl ethers (e.g., diethyl ether), or cyclic ethers (such as tetrahydrofuran).

The time and temperature of reaction may vary from as little as about 1 hour (or even less) at elevated temperature conditions, such as above about 60° C. (like about 100° C.), to about overnight (such as about 18 to about 24 hours) at lower temperatures, such as about room temperature, where no added heat source is provided.

The alkyl, alkenyl, alkynyl or aryl formyl acetate formed in step (a) above (and optionally separated in step (b) above) may be selected from methyl formyl acetate, ethyl formyl acetate, propyl formyl acetates, butyl formyl acetates, pentyl formyl acetates, hexyl formyl acetates, heptyl formyl acetates, octyl formyl acetates, allyl formyl acetate, propargyl formyl acetate, phenyl formyl acetate, phenethyl formyl acetate, or benzyl formyl acetate, to name a few.

To form cyanoacetates from any of these alkyl, alkenyl, alkynyl or aryl formyl acetates, hydroxyl amine acids should be used.

The hydroxyl amine acids may be selected from hydroxyl amine hydrochloride, hydroxyl amine sulfur dioxide, hydroxyl amine sulfuric acid, and combinations thereof.

The amount of the hydroxyl amine acid may be less than about equimolar or more than about equimolar relative to the alkyl, alkenyl, alkynyl or aryl formyl acetate. As little as about 0.25 to about less than half of a molar equivalent of the hydroxyl amine acid may be used and as much as about 1.5 molar equivalents of the hydroxyl amine acid may be used.

The reaction should be conducted under acidic conditions. To that end, a mineral acid (like hydrochloric acid) or an organic acid (like acetic acid) should be used. The amount of acid should be sufficient to reduce the pH to below 7, such as below about 4, desirably below about 3, more desirably below about 2.

The appropriate conditions may comprise the use of an organic polar solvent, such as an organic polar protic solvent. Desirable choices for such a solvent are alcohols, such as methanol and ethanol.

The time and temperature of reaction may vary from as little as about 1 hour (or even less) at elevated temperature conditions, such as about 90° C. to about overnight (such as about 18 to about 24 hours) at that temperature.

The cyanoacetate formed in this manner may be any of a $C_{1-20}$ alkyl cyanoacetate, a $C_{6-20}$ aryl cyanoacetate, a $C_{7-20}$ alkaryl cyanoacetate or a $C_{7-20}$ aralkyl cyanoacetate, any of which may be substituted by one or more hydroxyl groups or $C_{1-20}$ alkyl ether groups. For instance, the cyanoacetate formed may be a $C_{1-20}$ alkyl cyanoacetate, where the $C_{1-20}$ alkyl may be straight chain or branched, contain one or more points of unsaturation and may be substituted and/or interrupted by one or heteroatoms or heteroatom-containing groups, or substituted by halogens or substituted or interrupted by halogen-containing groups (such as trimethylsilyl alkyl, like methyl, ethyl or propyl), or substituted by halogens or substituted or interrupted by halogen-containing groups.

Thus, the cyanoacetate may be methyl, ethyl, propyls (like n-propyl or iso-propyl), propargyl, butyls (like n-butyl or iso-butyl), pentyls (like n-pentyl or iso-amyl), hexyl, octyls (like n-octyl or 2-ethylhexyl), nonyl, oxononyl, decyl, dodecyl, allyl, ethynyl, butenyl, cyclohexyl, tetrahydrofurfuryl, chloroethyl, 2,2,2-trifluoroethyl, hexafluoroisopropyl, alkoxy ether alkyl cyanoacetates (such as methoxymethyl, methoxyethyl, methoxybutyl, ethoxyethyl, propoxyethyl, butoxymethyl, or butoxyethyl) and dimethyl siloxane esters of 2-cyanoacetic acid. This recitation is by no means however exhaustive.

The cyanoacetate may also be a $C_{6-20}$ aryl cyanoacetate, such as phenyl cyanoacetate.

Or, the cyanoacetate may be a $C_{7-20}$ aralkyl cyanoacetate selected from phenethyl cyanoacetate, benzyl cyanoacetate, or toluyl cyanoacetate.

The separation step(s) should yield product substantially free from the reactants and by-products.

In another aspect, a process for the preparation of a cyanoacetate is provided that includes one step. The step of the process comprises:

contacting a salt of an alkyl, alkenyl, alkynyl or aryl formyl acetate with a hydroxyl amine acid under appropriate conditions and for a time sufficient to yield a cyanoacetate. Optionally, the so formed cyanoacetate may be separated therefrom.

In yet another aspect, a process for the preparation of a cyanoacetate is provided that includes one step. The step of the process comprises:

contacting an alkyl, alkenyl, alkynyl or aryl acetate with an alkyl, alkenyl, alkynyl or aryl formate with a base and for a time sufficient to form a salt of an alkyl, alkenyl, alkynyl or aryl formyl acetate, and after which mixing therewith a hydroxyl amine acid under appropriate conditions and for a time sufficient to yield a cyanoacetate. Optionally, the so formed cyanoacetate may be separated therefrom.

Here, like above, the alkyl, alkenyl, alkynyl or aryl formyl acetate is selected from methyl formyl acetate, ethyl formyl acetate, propyl formyl acetates, butyl formyl acetates, pentyl formyl acetates, hexyl formyl acetates, heptyl formyl acetates, octyl formyl acetates, allyl formyl acetate, propargyl formyl acetate, phenyl formyl acetate, phenethyl formyl acetate, or benzyl formyl acetate.

As above, the cyanoacetate is a $C_{1-20}$ alkyl cyanoacetate, a $C_{6-20}$ aryl cyanoacetate, a $C_{7-20}$ alkaryl cyanoacetate or a $C_{7-20}$ aralkyl cyanoacetate, any of which may be substituted by one or more hydroxyl groups or $C_{1-20}$ alkyl ether groups. The $C_{1-20}$ alkyl may contain one or more points of unsaturation and may be substituted and/or interrupted by one or heteroatoms or heteroatom-containing groups, or substituted by halogens or substituted or interrupted by halogen-containing groups.

The cyanoacetate thus may be a $C_{1-20}$ alkyl cyanoacetate selected from methyl cyanoacetate, ethyl cyanoacetate, propyl cyanoacetates, butyl cyanoacetates, pentyl cyanoacetates, octyl cyanoacetates, alkoxy ether alkyl cyanoacetates, allyl cyanoacetates, and combinations thereof. Or the cyanoacetate may be a $C_{6-20}$ aryl cyanoacetate, such as phenyl cyanoacetate. The cyanoacetate may also be a $C_{1-20}$ aralkyl cyanoacetate selected from phenethyl cyanoacetate, benzyl cyanoacetate, or toluyl cyanoacetate.

The process step (b) [or steps (b) and (d)] should be substantially free from the reactants and/or by-products.

While the time of reaction is generally given above, the time may be monitored by reference to the formation of the desired product using NMR spectrometry, as noted in the Examples. The time of reaction may be adjusted depending on the identity of the specific reactants, the scale of the reaction and whether heat is added to the reaction conditions.

The following examples are intended to illustrate but in no way limit the present invention.

EXAMPLES

Example 1

Two-Step Reaction

A. Synthesis of Enol Sodium Salt from Ethyl Formyl Acetate (EFA) and Ethyl Acetate (EA)

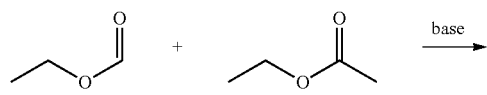

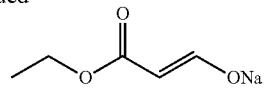

In an oven dried 1 L three necked flask under inert atmosphere equipped with a reflux condenser and a $N_2$ balloon, a base (e.g., sodium hydride, sodium methoxide or sodium ethoxide, or the potassium counterparts thereof) was added. An organic solvent comprising ethyl acetate with or without another solvent (e.g., diethyl ether or THF) was added followed by dropwise addition of ethyl formate (or methyl formate) over a period of 10 minutes at room temperature. The resulting suspension was diluted with diethyl ether (50 mL for 35 mmol of base), after which it was filtered and washed again with diethyl ether (50 mL) and dried in vacuo to obtain the enol salt as an off-white solid. $^1$H-NMR (60 MHz, $D_2O$): δ 8.63 (br, 1H), 4.08 (q, J=7.2 Hz, 2H), 1.23 (t, J=7.2 Hz, 3H).

TABLE 1

Optimisation of the reaction conditions for the formation of enol sodium salt

| Entry | Base | EtOAc | alkyl formate | Solv. (M) | T (h) | Yield (%) |
|---|---|---|---|---|---|---|
| 1 | NaH (1.15 eq) | 1.0 eq | ethyl formate (1.15 eq) | THF (0.5) | 20 | 29 |
| 2 | NaH (1.15 eq) | 1.0 eq | ethyl formate (1.15 eq) | Et$_2$O (1.5) | 21 | 78 |
| 3 | NaH (1.15 eq) | 5.0 eq | methyl formate (1.15 eq) | — | 2 | 29 |
| 4 | NaH (1.0 eq) | 0.6 eq | ethyl formate (0.6 eq) | Et$_2$O (1.6) | 18 | 51 |
| 5 | NaH (1.0 eq) | 0.5 eq | ethyl formate (0.6 eq) | Et$_2$O (2.9) | 18 | 80 |
| 6 | NaOEt (1.0 eq) | 1.0 eq | ethyl formate (1.0 eq) | EtOH (1.7) | 18 | Trace |
| 7 | NaOEt (1.0 eq) | 1.0 eq | ethyl formate (1.0 eq) | CH$_3$CN (3.0) | 3 | Trace |
| 8 | NaOEt (1.0 eq) | 1.0 eq | ethyl formate (1.0 eq) | Et$_2$O (1.7) | 18 | 56 |
| 9 | NaOEt (1.0 eq) | 2.6 eq | ethyl formate (1.0 eq) | — | 18 | 55 |
| 10 | NaOEt (1.0 eq) | 3.3 eq | ethyl formate (1.0 eq) | — | 18 | 50 |
| 11 | NaOEt (1.0 eq) | 2.6 eq | ethyl formate (1.0 eq) | — | 3.3 | 54 |
| 12 | NaOEt (1.0 eq) | 2.6 eq | ethyl formate (1.25 eq) | — | 3 | 49 |
| 13 | NaOEt (1.0 eq) | 1.0 eq | ethyl formate (1.5 eq) | — | 3 | 39 |
| 14 | NaOEt (1.0 eq) | 3.4 eq | ethyl formate (1.0 eq) | — | 18 | 50 |
| 15 | NaOEt (1.0 eq) | 3.4 eq | ethyl formate (1.0 eq) | — | 5 | 53 |
| 16 | NaOEt (1.0 eq) | 2.0 eq | ethyl formate (2.0 eq) | — | 5 | 43 |
| 17 | NaOEt (1.0 eq) | 3.4 eq | ethyl formate (2.0 eq) | — | 4 | 50 |
| 18 | NaOEt (1.0 eq) | 3.4 eq | ethyl formate (1.0 eq) | — | 4 | 52 |
| 19 | NaOMe (1.0 eq) | 3.4 eq | ethyl formate (1.0 eq) | — | 4 | 56 |

In Table 1, preliminary reactions are recorded with sodium hydride as a base (Entries 1-5). While the reaction was successful when THF was used as a solvent (Entry 1), the yields were poor. When diethyl ether was used as a solvent, then the yield improved and the salt was isolated (Entry 2). When excess sodium hydride was used as a base under concentrated reaction conditions (2.9 M), the yield of the salt improved (Entry 5).

Sodium ethoxide was also used as a base instead of sodium hydride. While initial results with ethanol or acetonitrile as a solvent were not satisfactory (Entries 6 and 7), with diethyl ether as the solvent the salt was isolated in a moderate yield (56%, Entry 10). When ethyl acetate was used, the reaction resulted in similar yields (55%, Entry 11).

B. Synthesis of ECnA from Enol Sodium Salt

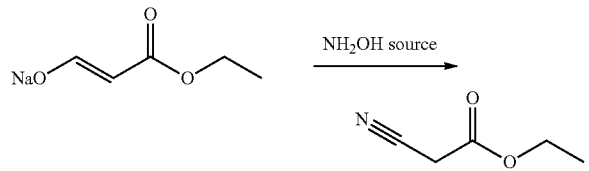

In an oven dried 500 mL round bottom flask equipped with a reflux condenser and a $N_2$ balloon, enol sodium salt (10.0 grams) was added followed by a solvent and $NH_2OH$ salt. The reaction mixture was heated to reflux for 10 minutes and then a Bronsted acid was added dropwise until the desired pH was achieved. The reaction mixture was further refluxed and then cooled to room temperature. The solids were filtered, washed with ethanol, and the combined filtrate was evaporated in a rotary evaporator to obtain the crude product. To the crude product 50.0 mL of distilled water was added and then extracted with chloroform (3×50 mL). The chloroform extract was washed with distilled water (2×50 mL) and then brine (2×50 mL), after which the extract was dried over $Na_2SO_4$ and evaporated to obtain crude product which was then purified by vacuum distillation (Pot temp.=60° C., cross head temp.=35° C., 0.45 mbar). $^1$H NMR (60 MHz, $CDCl_3$): δ 4.18 (q, J=6.6 Hz, 2H), 3.42 (s, 2H), 1.24 (t, J=6.6 Hz, 3H).

under acidic conditions, ethyl cyanoacetate was isolated after extraction with chloroform and water in 69% yield (Entry 4). The yields were improved to 81% when equimolar quantities of hydroxylamine hydrochloride were used (Entry 5). When excess solvent was used, the yield of ethyl cyanoacetate also improved (cf. Entry 5 and Entry 6).

What is claimed is:

1. A process for the preparation of a cyanoacetate, steps of which comprise:
    (a) contacting an alkyl, alkenyl, alkynyl or aryl acetate with an alkyl, alkenyl, alkynyl or aryl formate in the presence of a base and for a time sufficient to form a salt of an alkyl, alkenyl, alkynyl or aryl formyl acetate;
    (b) optionally, separating therefrom the so formed salt of the alkyl, alkenyl, alkynyl or aryl formyl acetate;
    (c) contacting the so formed salt of the alkyl, alkenyl, alkynyl or aryl formyl acetate with a hydroxyl amine acid under appropriate conditions and for a time sufficient to yield a cyanoacetate;
    (d) optionally, separating therefrom the so formed cyanoacetate.

2. The process of claim 1, wherein the conditions of step (a) comprise in an organic polar solvent or an organic polar protic solvent.

3. The process of claim 1, wherein the conditions of step (a) comprise at room temperature.

4. The process of claim 1, wherein the alkyl, alkenyl, alkynyl or aryl acetate is selected from methyl acetate, ethyl acetate, propyl acetates, butyl acetates, pentyl acetates, hexyl acetates, heptyl acetates, octyl acetates, allyl acetate, propargyl acetate, phenyl acetate, phenethyl acetate, or benzyl acetate.

5. The process of claim 1, wherein the alkyl, alkenyl, alkynyl or aryl formate is selected from methyl formate, ethyl formate, propyl formates, butyl formates, pentyl formates, hexyl formates, heptyl formates, octyl formates, allyl formate, propargyl formate, phenyl formate, phenethyl formate, or benzyl formate.

6. The process of claim 1, wherein the basic conditions are formed from sodium hydride, potassium hydride, sodium alkoxide, potassium alkoxide, and combinations thereof.

TABLE 2

Optimisation of the reaction conditions for the formation of ECnA

| Entry | Enol | $NH_2OH$ source | Acid (pH) | Solv. (M) | T (h) | Temp. (° C.) | Yield (%) |
|---|---|---|---|---|---|---|---|
| 1 | 7.2 mmol | $NH_2OH\cdot HCl$ (1.0 eq) | — | $H_2O$ (0.36M) | 18 | rt | — |
| 2 | 7.2 mmol | $NH_2OH\cdot HCl$ (1.0 eq) | HCl (pH = 7) | $H_2O$ (0.36M) | 18 | rt | — |
| 3 | 7.2 mmol | $NH_2OH\cdot HCl$ (1.0 eq) | HCl (pH = 2) | $H_2O$ (0.36M) | 18 | rt | — |
| 4 | 7.2 mmol | $NH_2OH\cdot HCl$ (1.5 eq) | HCl (pH = 2) | EtOH (0.3M) | 4 | 90 | 69 |
| 5 | 7.2 mmol | $NH_2OH\cdot HCl$ (1.0 eq) | HCl (pH = 2) | EtOH (0.3M) | 4 | 90 | 81 |
| 6 | 76 mmol | $NH_2OH\cdot HCl$ (1.0 eq) | HCl (pH = 2) | EtOH (0.7M) | 4 | 90 | 55 |
| 7 | 71 mmol | $NH_2OH\cdot HCl$ (1.0 eq) | AcCl (pH = 2) | EtOH (0.7M) | 4 | 90 | 63 |
| 8 | 7.2 mmol | $NH_2OH\cdot HCl$ (1.0 eq) | HCl (pH = 1) | EtOH (0.6M) | 4 | 90 | 54 |
| 9 | 197 mmol | $NH_2OH\cdot HCl$ (1.0 eq) | HCl (pH = 4) | Dry EtOH (0.4M) | 18 | 90 | 46 |
| 10 | 7.2 mmol | $NH_2OH\cdot HCl$ (1.0 eq) | HCl (pH = 2) | EtOH (0.3M) | 2 | 90 | 43 |
| 11 | 7.2 mmol | $NH_2OH\cdot HCl$ (1.0 eq) | HCl (pH = 2) | EtOH (0.3M) | 3 | 90 | 50 |
| 12 | 7.2 mmol | $NH_2OH\cdot HCl$ (1.0 eq) | HCl (pH = 2) | EtOH (0.3M) | 1 | 90 | 48 |
| 13 | 7.2 mmol | $NH_2OSO_3H$ (1.0 eq) | HCl (pH = 2) | EtOH (0.3M) | 4 | 90 | 62 |
| 14 | 7.2 mmol | $NH_2OSO_3H$ (1.5 eq) | HCl (pH = 2) | EtOH (0.3M) | 4 | 90 | 66 |
| 15 | 7.2 mmol | $NH_2OSO_3H$ (1.0 eq) | AcOH (pH = 4) | EtOH (0.3M) | 4 | 90 | 64 |
| 16 | 50 mmol | $(NH_2OH)_2\cdot H_2SO_4$ (1.0 eq) | HCl (pH = 2) | EtOH (0.7M) | 4 | 90 | 21 |

When a mixture of enol salt and hydroxyl amine hydrochloride (in excess) was heated to reflux in absolute ethanol 7. The process of claim 1, wherein the salt of an alkyl, alkenyl, alkynyl or aryl formyl acetate is selected from the sodium or potassium salt of the enol structure of methyl formyl acetate, ethyl formyl acetate, propyl formyl acetates, butyl formyl acetates, pentyl formyl acetates, hexyl formyl acetates, heptyl formyl acetates, octyl formyl acetates, allyl formyl acetate, propargyl formyl acetate, phenyl formyl acetate, phenethyl formyl acetate, or benzyl formyl acetate.

8. The process of claim 1, wherein the hydroxyl amine acid is selected from hydroxyl amine hydrochloride or hydroxyl amine sulfur trioxide.

9. The process of claim 1, wherein the cyanoacetate is a $C_{1-20}$ alkyl cyanoacetate, a $C_{6-20}$ aryl cyanoacetate, a $C_{7-20}$ alkaryl cyanoacetate or a $C_{7-20}$ aralkyl cyanoacetate, any of which may be substituted by one or more hydroxyl groups or $C_{1-20}$ alkyl ether groups.

10. The process of claim 1, wherein the cyanoacetate is a $C_{1-20}$ alkyl cyanoacetate, wherein the $C_{1-20}$ alkyl may contain one or more points of unsaturation and may be substituted and/or interrupted by one or one heteroatoms or heteroatom-containing groups, or substituted by halogens or substituted or interrupted by halogen-containing groups.

11. The process of claim 1, wherein the cyanoacetate is a $C_{1-20}$ alkyl cyanoacetate selected from methyl cyanoacetate, ethyl cyanoacetate, propyl cyanoacetates, butyl cyanoacetates, pentyl cyanoacetates, octyl cyanoacetates, alkoxy ether alkyl cyanoacetates, allyl cyanoacetates, and combinations thereof.

12. The process of claim 1, wherein the cyanoacetate is a $C_{6-20}$ aryl cyanoacetate.

13. The process of claim 1, wherein the cyanoacetate is phenyl cyanoacetate.

14. The process of claim 1, wherein the cyanoacetate is a $C_{7-20}$ aralkyl cyanoacetate selected from phenethyl cyanoacetate, benzyl cyanoacetate, or toluyl cyanoacetate.

15. The process of claim 1, wherein step (b) is substantially free from starting materials and/or by-products.

16. The process of claim 1, wherein step (d) is substantially free from starting materials and/or by-products.

17. A process for the preparation of a cyanoacetate, steps of which comprise:
(i) contacting a salt of an alkyl, alkenyl, alkynyl or aryl formyl acetate with a hydroxyl amine acid under appropriate conditions and for a time sufficient to yield a cyanoacetate;
(ii) optionally, separating therefrom the so formed cyanoacetate.

18. A process for the preparation of a cyanoacetate, steps of which comprise:
(i) contacting an alkyl, alkenyl, alkynyl or aryl acetate with an alkyl, alkenyl, alkynyl or aryl formate with a base and for a time sufficient to form a salt of an alkyl, alkenyl, alkynyl or aryl formyl acetate, and after which mixing therewith a hydroxyl amine acid under appropriate conditions and for a time sufficient to yield a cyanoacetate;
(ii) optionally, separating therefrom the so formed cyanoacetate.

19. The process of claim 17, wherein the hydroxyl amine acid is selected from hydroxyl amine hydrochloride or hydroxyl amine sulfur trioxide.

* * * * *